(12) United States Patent
Chen

(10) Patent No.: US 7,335,211 B2
(45) Date of Patent: Feb. 26, 2008

(54) TRANSMISSION SYSTEM OF EYEBROW-BEAUTIFYING DEVICE

(76) Inventor: Cheng-Kun Chen, P.O. Box 1-79, Taipei (TW) 100

( * ) Notice: Subject to any disclaimer, the term of this patent is extended or adjusted under 35 U.S.C. 154(b) by 3 days.

(21) Appl. No.: 10/690,673

(22) Filed: Oct. 23, 2003

(65) Prior Publication Data

US 2004/0143275 A1    Jul. 22, 2004

(30) Foreign Application Priority Data

Jan. 20, 2003    (TW) ............................. 92201002 U

(51) Int. Cl.
*A61B 17/50*    (2006.01)
(52) U.S. Cl. ..................................... 606/133
(58) Field of Classification Search .............. 606/133, 606/187, 36, 43, 44
See application file for complete search history.

(56) References Cited

U.S. PATENT DOCUMENTS

| 2,110,735 A | * | 3/1938 | Marton | 606/44 |
| 2,994,324 A | * | 8/1961 | Lemos | 606/44 |
| 3,035,580 A | * | 5/1962 | Guiorguiev | 606/44 |
| 3,651,812 A | * | 3/1972 | Samuels | 606/44 |
| 4,423,837 A | * | 1/1984 | Clements | 227/67 |
| 5,221,280 A | * | 6/1993 | Gross et al. | 606/36 |

FOREIGN PATENT DOCUMENTS

| TW | 111055 | 4/1989 |
| TW | 160146 | 6/1991 |

* cited by examiner

*Primary Examiner*—Eduardo C. Robert
*Assistant Examiner*—Michael J Araj

(57) ABSTRACT

A transmission system of eyebrow-beautifying device is disclosed. A lever member has two contacts at bottoms of both sides. The contacts rest on a periphery of a wear-resistant member. A pivot point of a transmission unit and the lever member is disposed above the contacts. A torque of the lever member is substantially the same as that of the transmission unit. A rate of wear between the lever member and the wear-resistant member is substantially the same as that between the transmission unit and the lever member. That is, no amplification of error or wear may exist therebetween. Hence, the prior drawback of deterioration of vibration of the motor shaft caused by serious wear of the action block is completely eliminated.

6 Claims, 9 Drawing Sheets

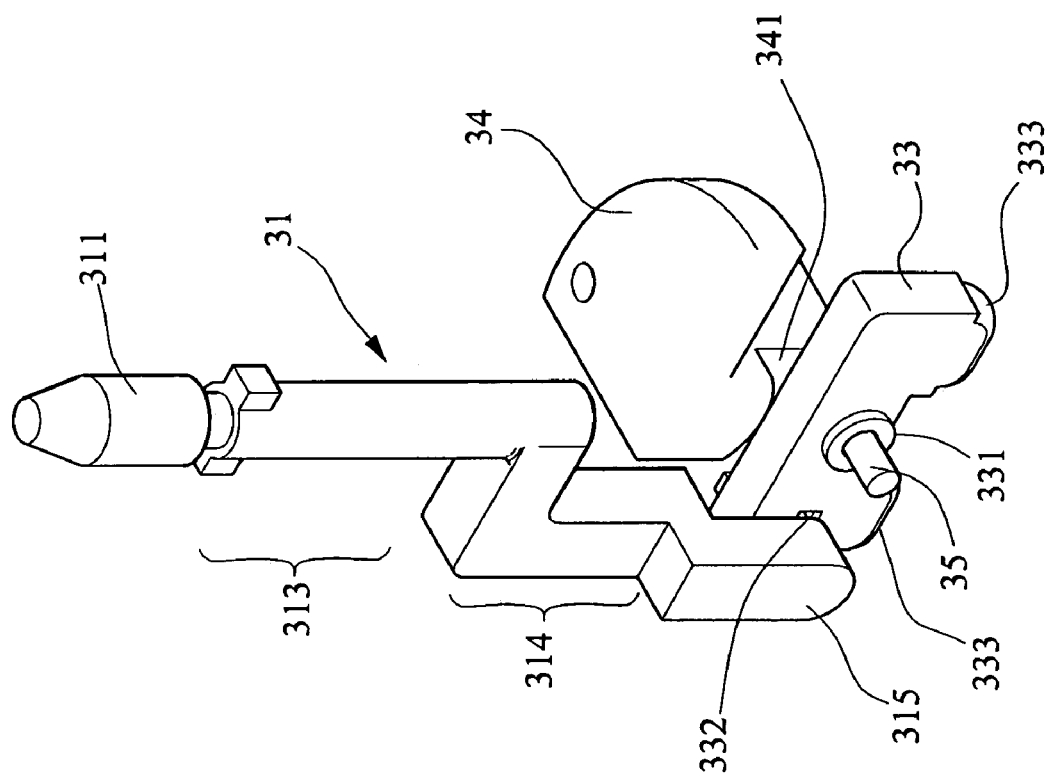
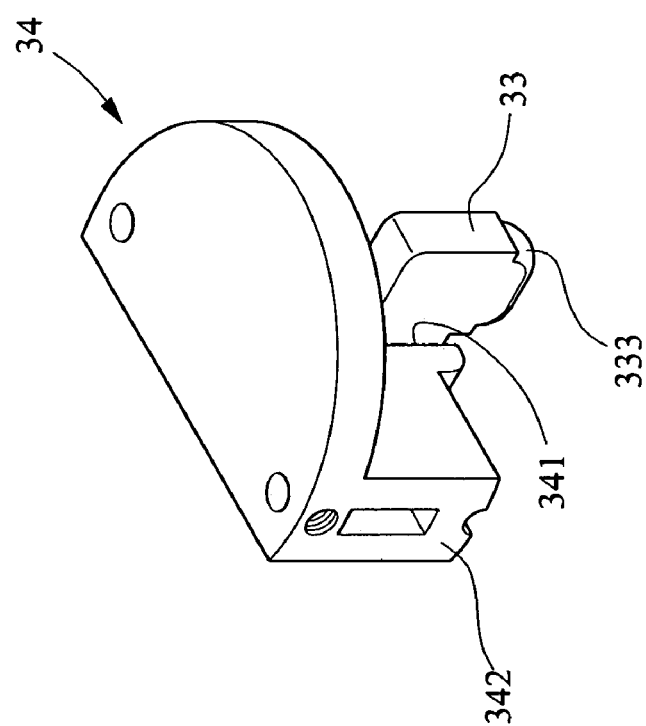

TRANSMISSION SYSTEM OF EYEBROW-BEAUTIFYING DEVICE

BACKGROUND OF THE INVENTION

1. Field of the Invention

The present invention relates to transmission and more particularly to an improved transmission system of an eyebrow-beautifying device.

2. Description of Related Art

A conventional transmission system of an eyebrow-beautifying device comprises a transmission member pivotably provided on a bracket on a motor. One end of the transmission member is driven by the motor so that the transmission member can operate by leverage. A link of needle is coupled to the other end of the transmission member. As such, the link of needle can move reciprocally, linearly by the action of cam. Thus, a used needle is required to remove prior to inserting a new one for replacement in such cam design. An insertion force of the needle will transmit to the transmission member directly. However, the transmission member is merely supported by a small fulcrum. Hence, it is possible that a bending torque can be created if the force is not balanced or excessively large. As an end, the transmission member is susceptible of damage. In another aspect, the transmission member or any of other components is typically formed of plastic for reducing the load of the motor. This can further tend to bend or even greatly wear the transmission member. Moreover, a distance from one end of the transmission member to the fulcrum and another distance from the other end to the fulcrum are different. Hence, torque is imbalance. Both ends of the transmission member may increase as the distances increase while the transmission member is operating by leverage when the motor is rotating. This in turn can cause excessive vibration of the motor, resulting in a reduction of motor output power and greatly wearing the transmission system.

A Taiwanese Patent Published No. 111,055 entitled "Improved Eyebrow-Beatifying Device" disclosed, as shown in FIGS. 2 to 5 thereof, a motor shaft 41 having an oblique top surface 42, an action block 6 supported on the oblique surface, and a link of needle 8 linearly, reciprocally moveable by means of frictional surface contact between the action block 6. Another Taiwanese Patent Published No. 160,146 entitled "Improved Transmission System of Eyebrow-Beatifying Device" disclosed, as shown in FIG. 1 thereof, a motor shaft 12 having an oblique top surface and an action block 13 supported on the oblique surface. Moreover, the linear movement by means of frictional surface contact as disclosed in Taiwanese Patent Published No. 111,055 is changed as a frictional line contact between the action block 13 and the oblique surface of the motor shaft 12. As an end, a link of needle 16 is able to move linearly, reciprocally.

Both Taiwanese Patents have contributed to the transmission system of eyebrow-beautifying device. However, both prior art still suffered from several disadvantages. For example, with respect to the transmission system of eyebrow-beautifying device, both disclosed an elongate transmission bar projected from the action block, and a link of needle coupled to the transmission bar. As such, the action block will operate by leverage for enabling the link of needle to move linearly, reciprocally when a frictional surface contact between the action block and the oblique surface of the motor shaft is carried out. As best seen from its figures, torque of the action block is much less than that between the transmission bar and the link of needle. Typically, torque between the transmission bar and the link of needle is about 2 to about 3 times larger than that of the action block. As such, for example, 0.1 m/m error between the action block and the oblique surface of the motor shaft due to wear will cause about 0.2 m/m to 0.3 m/m or larger error in the moving distance of the link of needle. As a consequence, a number of disadvantages are found such as abnormal vibration during operation, lowering mechanical efficiency, excessive wear of components, and shortening of useful life of the transmission system.

With respect to the transmission system of eyebrow-beautifying device, both disclosed an elongate transmission bar projected from the action block, and a link of needle coupled to the transmission bar. But there is no support under the transmission bar. Thus, a used needle is required to remove prior to inserting a new one for replacement. But an insertion force of the needle will transmit to the transmission bar directly. Hence, the transmission bar tends to be deformed or even broken (i.e., shortened useful life) after a short period of time of operation. Moreover, abnormal vibration during operation and lowering mechanical efficiency of the transmission system are found. In another aspect, the transmission member or any of other components is typically formed of plastic for reducing the load of the motor. This can further tend to bend and greatly wear the transmission member or even damage other adjacent, coupled components. Thus, the need for improvement still exists.

SUMMARY OF THE INVENTION

It is an object of the present invention to provide a transmission system of an eyebrow-beautifying device in which improvements have been made with respect to transmission members and transmission for making torque of the action block to be equal to that between the transmission bar and the link of needle in order to carry out a transmission of balanced torque. By utilizing the present invention, wear of components of the transmission system of the eyebrow-beautifying device can be reduced significantly and useful life of the eyebrow-beautifying device can be prolonged greatly.

It is another object of the present invention to provide a transmission system of an eyebrow-beautifying device in which distance between the transmission bar and the link of needle is reduced significantly so that a connecting point therebetween is disposed on top of the slanted seat and a support is formed under the link of needle when replacing the needle on top of the link. By utilizing the present invention, the prior drawbacks of deformation or even breakage and shortening of useful life of the link of needle after a short period of time of operation can be overcome.

To achieve the above and other objects, the present invention provides a transmission system of an eyebrow-beautifying device, comprising a joining member including a lower section having a longitudinal cut, the joining member being coupled to a lower post of a needle assembly, the needle assembly further including a needle projected upward from the post and a top sleeve for permitting the needle to either project therefrom or retract thereinto; a substantially zigzag transmission unit including a top section coupled to the lower section and a bottom connecting member; a connecting unit including two vertical sections at both sides, a horizontal section, a central slot, and a pivot hole through the slot; a lever member including a first aperture, a keyhole coupled to the connecting member, and two contacts at bottoms of both sides, the lever member being pivotably disposed in the slot by inserting a pin through the pivot hole; a slanted seat including a lower shaft sleeve; a replaceable wear-resistant member on the slanted seat; a motor including a shaft projected from a top and two diametrically disposed projections on the top; and a cylinder having a C-shaped section and including a central hole on a bottom for permitting the shaft sleeve to pass through to be fastened around the shaft, and two diametrically disposed second apertures on the bottom, the second apertures being adapted to snugly receive the projections when the cylinder is rested on the motor, whereby a rotation of the shaft will rotate the slanted seat for moving the transmission unit up and down cyclically and projecting the needle from the top sleeve and retract thereinto cyclically.

The above and other objects, features and advantages of the present invention will become apparent from the following detailed description taken with the accompanying drawings.

BRIEF DESCRIPTION OF THE DRAWINGS

FIG. 2A is a perspective view of connecting unit and lever member;

FIG. 2B is a perspective view in part section of the coupled transmission unit, connecting unit, lever member, and pin;

DETAILED DESCRIPTION OF THE PREFERRED EMBODIMENTS

Figure 1:
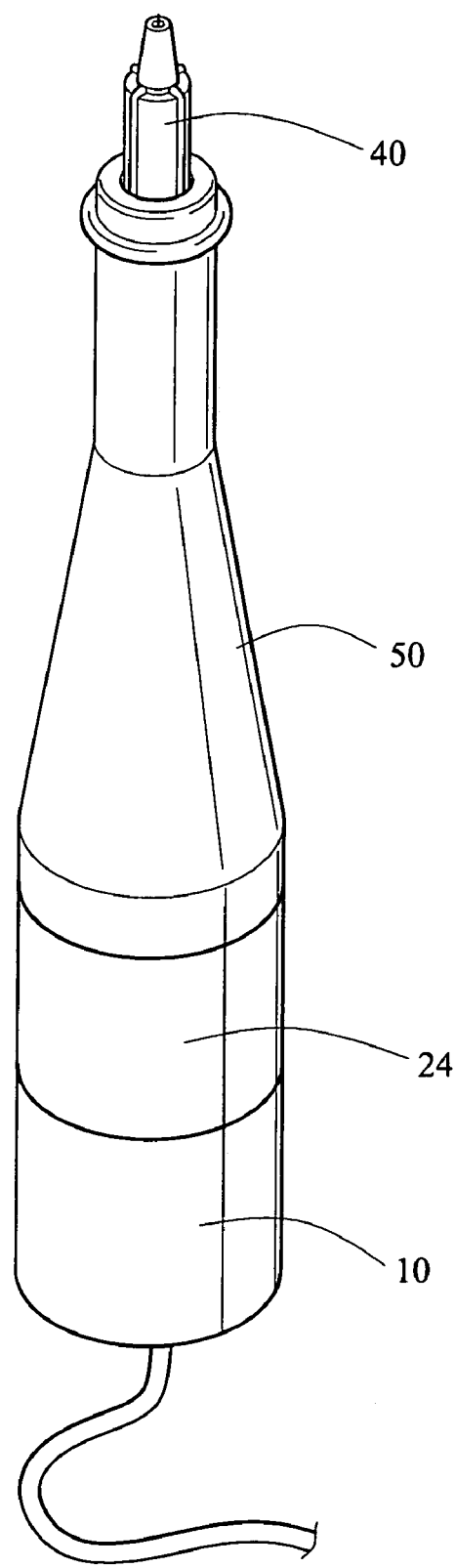
FIG. 1 is a perspective view of an eyebrow-beautifying device incorporating a first preferred embodiment of transmission system according to the invention.
Figure 2:
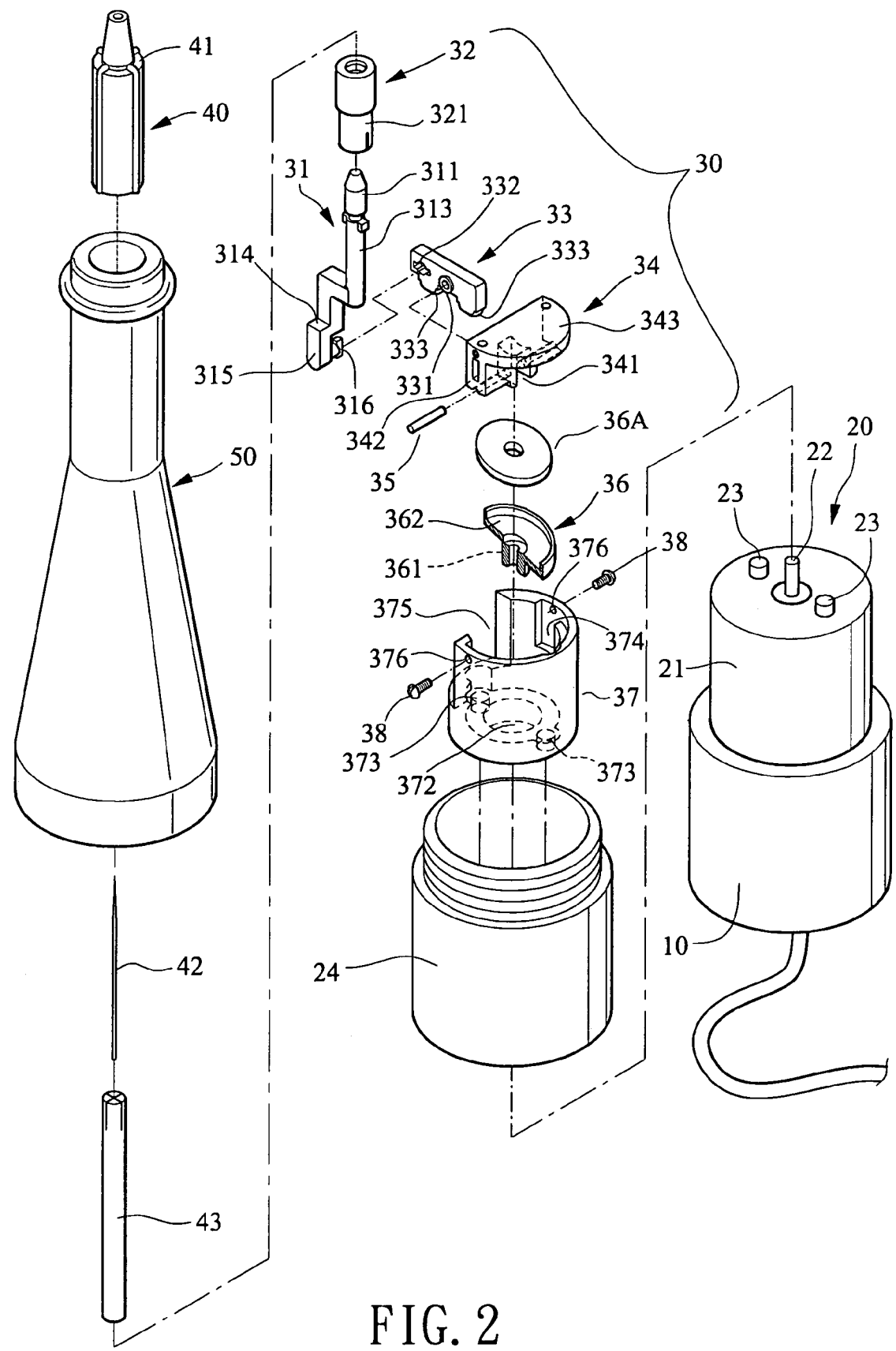
FIG. 2 is an exploded perspective view of FIG. 1.

Referring to FIGS. 1 to 7, there is shown an eyebrow-beautifying device incorporating a first preferred embodiment of transmission system in accordance with the invention. The eyebrow-beautifying device comprises a rotary switch 10, a motor 20 including a shaft 22 and a connecting sleeve 24, a transmission system 30, a cap 50 having a longitudinal channel, and a needle assembly 40 fastened at the mouth of the longitudinal channel of the cap 50, the needle assembly 40 including a lower post 43 moveable back and forth along the longitudinal channel, a needle 42 projected upward from the post 43, and a top sleeve 41 for permitting the needle 42 to either project from the mouth of the longitudinal channel or retract thereinto as the transmission system activates. However, only the transmission system 30 is a subject of the invention and other components are well known. Thus a detailed description these well known components is omitted herein for the sake of brevity.

The transmission system 30 comprises a transmission unit 31, a joining member 32 including a lower section 321 having a longitudinal cut, a lever member 33, a connecting unit 34, a pin 35, a wear-resistant member 36A, a slanted seat 36, and a cylinder 37 having a C-shaped section. Each component will be described in detail below.

The transmission unit 31 is a substantially zigzag configuration and comprises a top section 311 coupled to the lower section 321 of the joining member 32, a first L-shaped section 313 connected to the lower portion of the top section 311, a second L-shaped section 314 connected to the lower portion of the first L-shaped section 313, a third L-shaped section 315 connected to the lower portion of the second L-shaped section 314, and a bottom connecting member 316 connected to the lower portion of the third L-shaped section 315 in which the vertical portion of the first L-shaped section 313 is parallel to the vertical portion of the second L-shaped section 314, the vertical portion of the second L-shaped section 314 is parallel to the vertical portion of the third L-shaped section 315. The connecting member 316 is extended laterally from a vertically oriented slit of the vertical portion of the third L-shaped section 315 which is extended laterally into the keyhole 332 for fastening, however, the horizontal portion of the first L-shaped section 313 is vertical to the horizontal portions of the second L-shaped section 314 and the third L-shaped section 315, in which the bottom connecting member 316 is integrally formed with the horizontal portion of the third L-shaped section 315. This forms a unitary transmission unit 31. The lever member 33 comprises a central aperture 331, a keyhole 332 at one side thereof, and two contacts 333 at bottoms of both sides. The connecting unit 34 comprises two vertical sections 342 at both sides, a horizontal section 343 on the top, a central slot 341 between two vertical sections 342 and a pivot hole through the bottom of the two vertical sections 342. The lever member 33 is pivotably disposed in the pivot hole and a central slot 341 of the connecting unit 34 by means of the pin 35. As shown in FIGS. 2A and 2B, particularly FIG. 2B, it is seen that the zigzag transmission unit 31 is coupled to the lever member 33 by the inserting the connecting member 316 into the keyhole 332. As such, the transmission unit 31 and the connecting unit 34 can be assembled together and both are perpendicular each other without involving the use of any other tools or fasteners. Hence, the assembly of the invention is characterized in its simplicity and quickness. The slanted seat 36 and the wear-resistant member 36A are separate components. Also, the slanted seat 36 and the wear-resistant member 36A having different wear-resistant properties in which the latter is less wear-resistant than the former. Hence, the wear-resistant member 36A tends to wear out. But the wear-resistant member 36A is replaceable. This is another characteristic of the invention.

The most important characteristics of the invention are detailed below. The left and right contacts 333 of the lever member 33 rest on the periphery of the wear-resistant member 36A, as shown in FIGS. 4 to 7. The pivot point of the transmission unit 31 and the lever member 33 is disposed above the contacts 333. The torque of the lever member 33 is the same as that of the transmission unit 31. The rate of wear between the lever member 33 and the wear-resistant member 36A is the same as that between the transmission unit 31 and the lever member 33. In other words, no amplification of error or wear may exist therebetween. Hence, the prior drawback of deterioration of vibration of the motor shaft caused by serious wear of the action block is completely eliminated. This is a great improvement of the transmission system of the invention. Moreover, the connecting point of the transmission unit 31 and the lever member 33 is disposed above the circular top surface of the slanted seat 36. Hence, the transmission unit 31 surely is supported by the slanted seat 36 thereunder (not without support as experienced in the prior art) when inserting a new needle 42 through the sleeve 41 into the post 43 for replacement. Thus, the transmission unit 31 does not tend to deform or break even after a long period of time of operation. This is another great improvement of the invention.

The cylinder 37 has a C-shaped section and comprises a central hole 372 on its bottom for permitting a lower shaft sleeve 361 of the slanted seat 36 to pass through to be fastened around the motor shaft 22. The cylinder 37 further comprises two diametrically disposed apertures 373 on the bottom, the apertures 373 being adapted to snugly receive two diametrically disposed projections 23 on top of the motor 20 when the cylinder 37 is rested on the motor 20 (i.e., no involvement of fasteners (e.g., screws) for fastening the cylinder 37 and the motor 20), and two diametrically disposed recesses 374 on the inner wall. In assembly, two vertical sections 342 of the connecting unit 34 are snugly fitted in the diametrically disposed recesses 374 prior to driving screws 38 through the lateral apertures 376 into the vertical sections 342 for fastening the connecting unit 34 and the cylinder 37 together.

Figure 3:
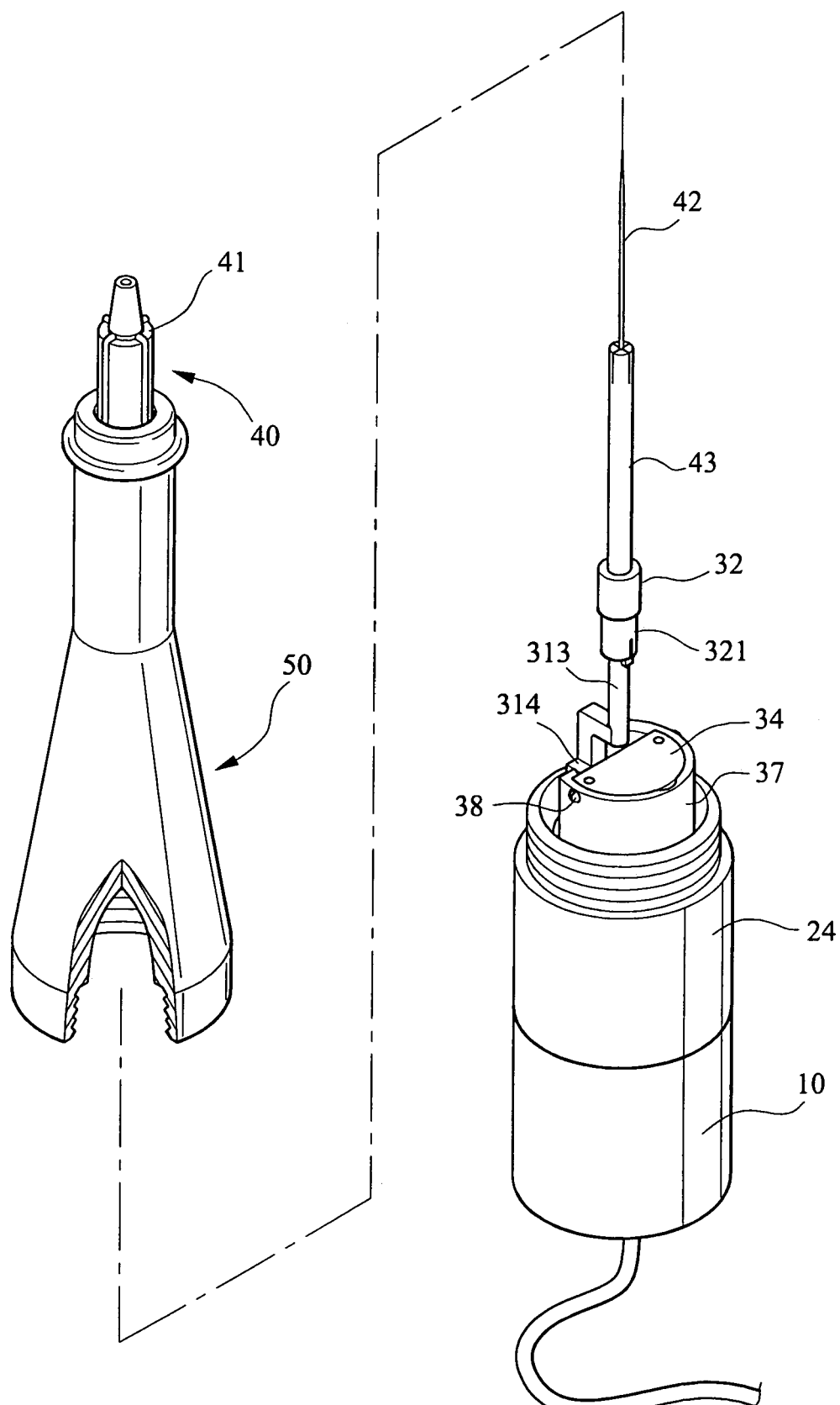
FIG. 3 is a perspective view of the eyebrow-beautifying device with the assembled needle assembly and cap separated.
Figure 4:
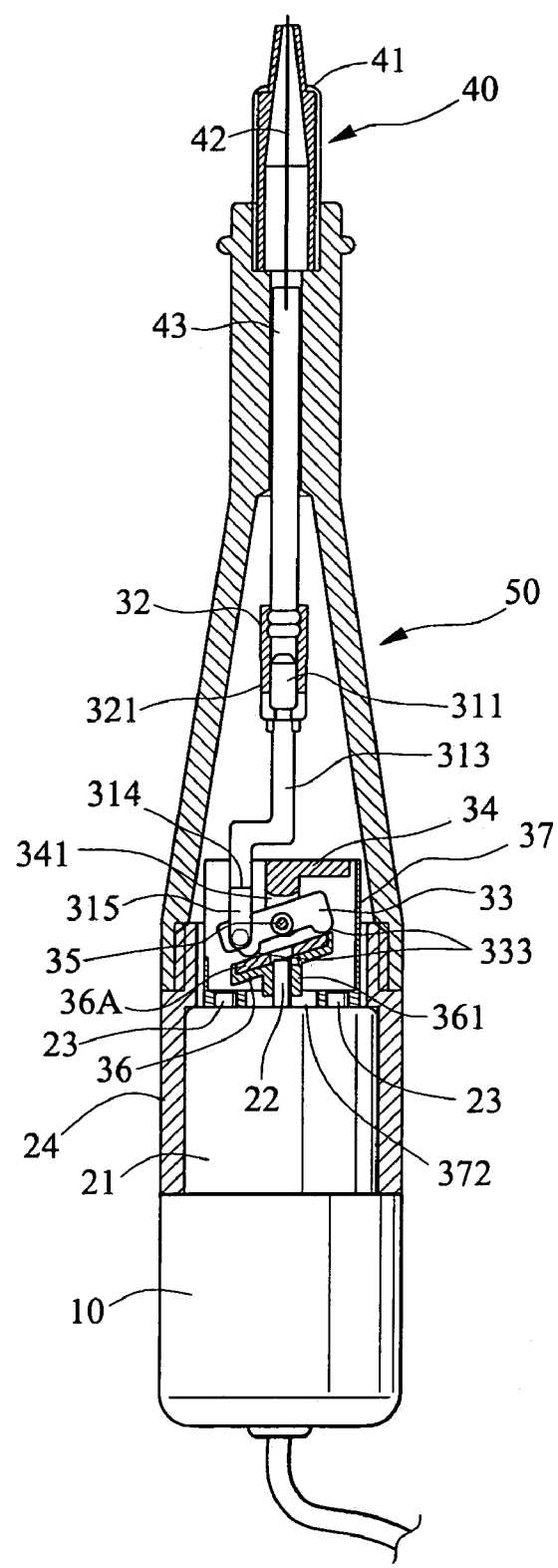
FIGS. 4 and 5 are cross-sectional views of FIG. 1 for illustrating two operational states of the transmission system.
Figure 5:
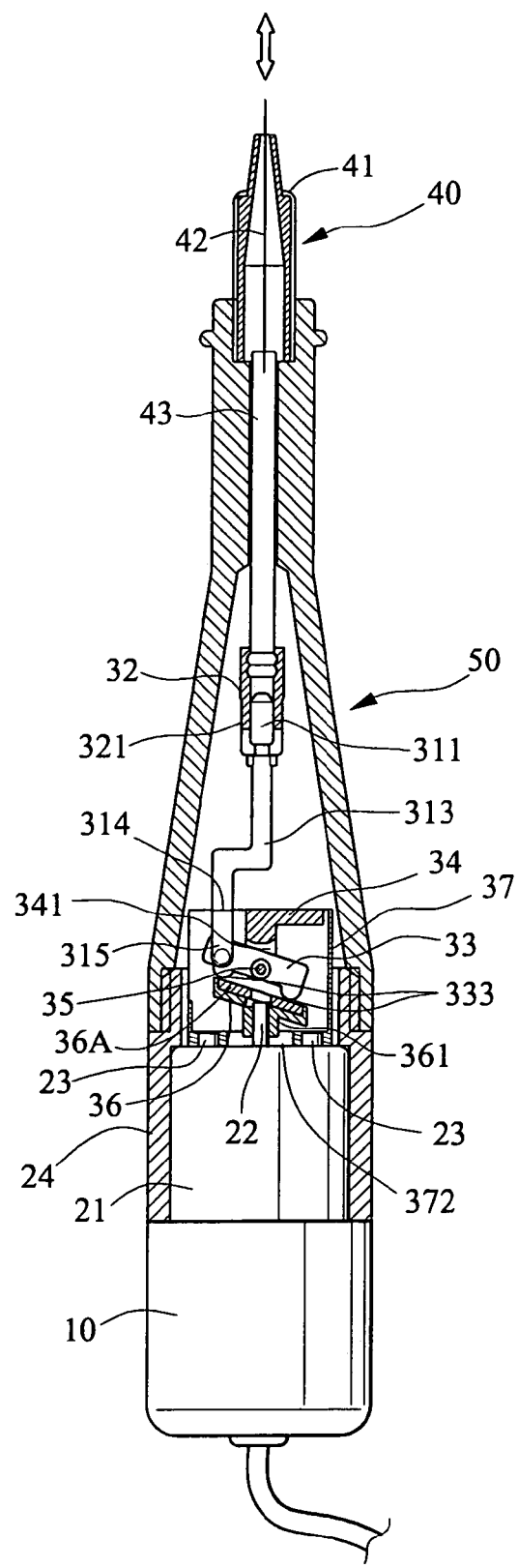

The transmission unit 31 and the lever member 33 are pivotably coupled together by inserting the pin 35 into the central slot 341 of the connecting unit 34 as devised by the transmission system of the eyebrow-beautifying device (see FIGS. 2A and 2B). At this moment, the slanted seat 36 fastened at the motor shaft 22 and the wear-resistant member 36A on the slanted seat 36 are received in the cylinder 37. Further, mount the lever member 33 on the wear-resistant member 36A. Next, mount the transmission unit 31 and the connecting unit 34 on the lever member 33 with the vertical sections 342 snugly fitted in the recesses 374 of the cylinder 37. Finally, fasten the connecting unit 34 and the cylinder 37 together by screws 38. This finishes the assembly of the transmission system of eyebrow-beautifying device (FIG. 3). In brief, the assembly of the transmission system 30 of the motor is done by simply coupling the transmission unit 31 and the lever member 33 together with both the lever member 33 and the connecting unit 34 being pivotably coupled together by means of the pin 35, and the connecting unit 34 fastened in the cylinder 37 by means of screws 38. In view of the above, it is very simple. Further, maintenance is also simple.

Figure 7:
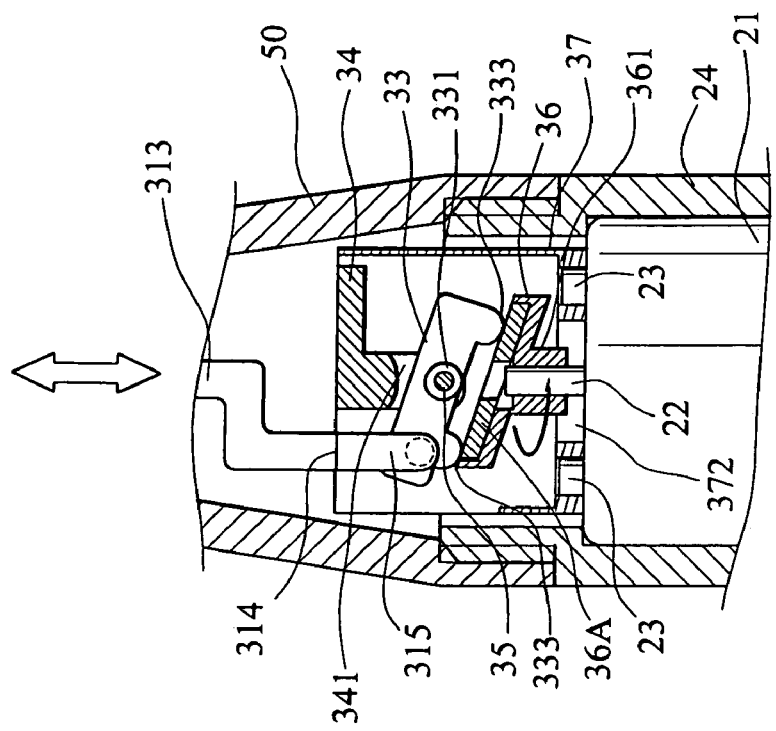
FIGS. 6 and 7 are greatly enlarged partial views of FIGS. 4 and 5 respectively.
Figure 6:
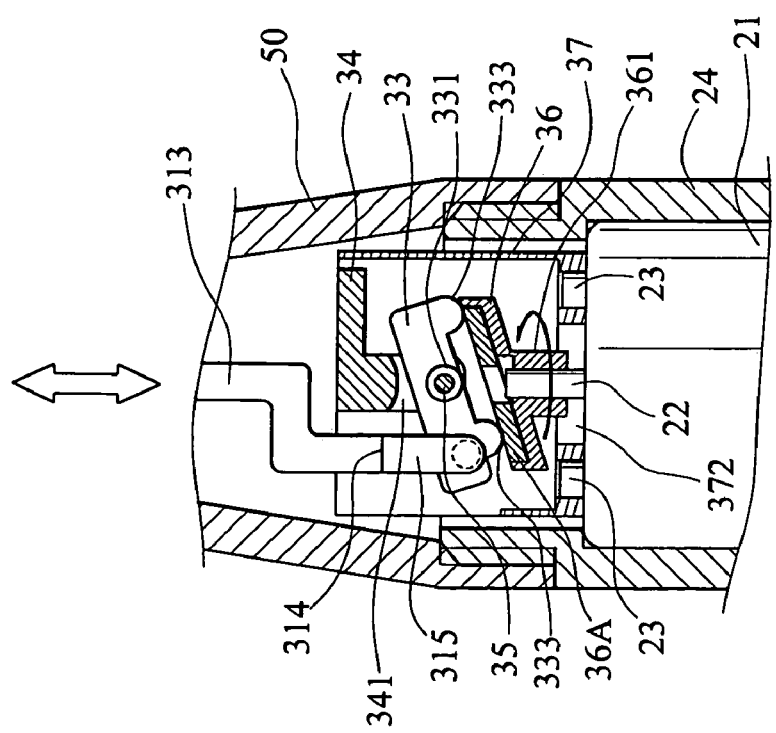

As best shown in FIGS. 6 and 7, a rotation of the motor 20 and thus the shaft 22 will rotate the slanted seat 36. Accordingly, the transmission unit 31 moves up and down cyclically. As an end, the needle 42 is adapted to project from top of the eyebrow-beautifying device and retract thereinto cyclically.

Note that components (e.g., the lever member 33 and the wear-resistant member 36A) of the transmission system 30 of the eyebrow-beautifying device of the invention are replaceable since they are susceptible of wear. Moreover, the bottom of the transmission unit 31 is supported by the wear-resistant member 36A and the slanted seat 36. Hence, the transmission unit 31 does not tend to deform. This arrangement can prolong a useful life of the eyebrow-beautifying device and reduce wear of the components to a minimum (i.e., nearly no malfunction). This is much advantageous over the well known transmission system of the eyebrow-beautifying device.

Figure 8:
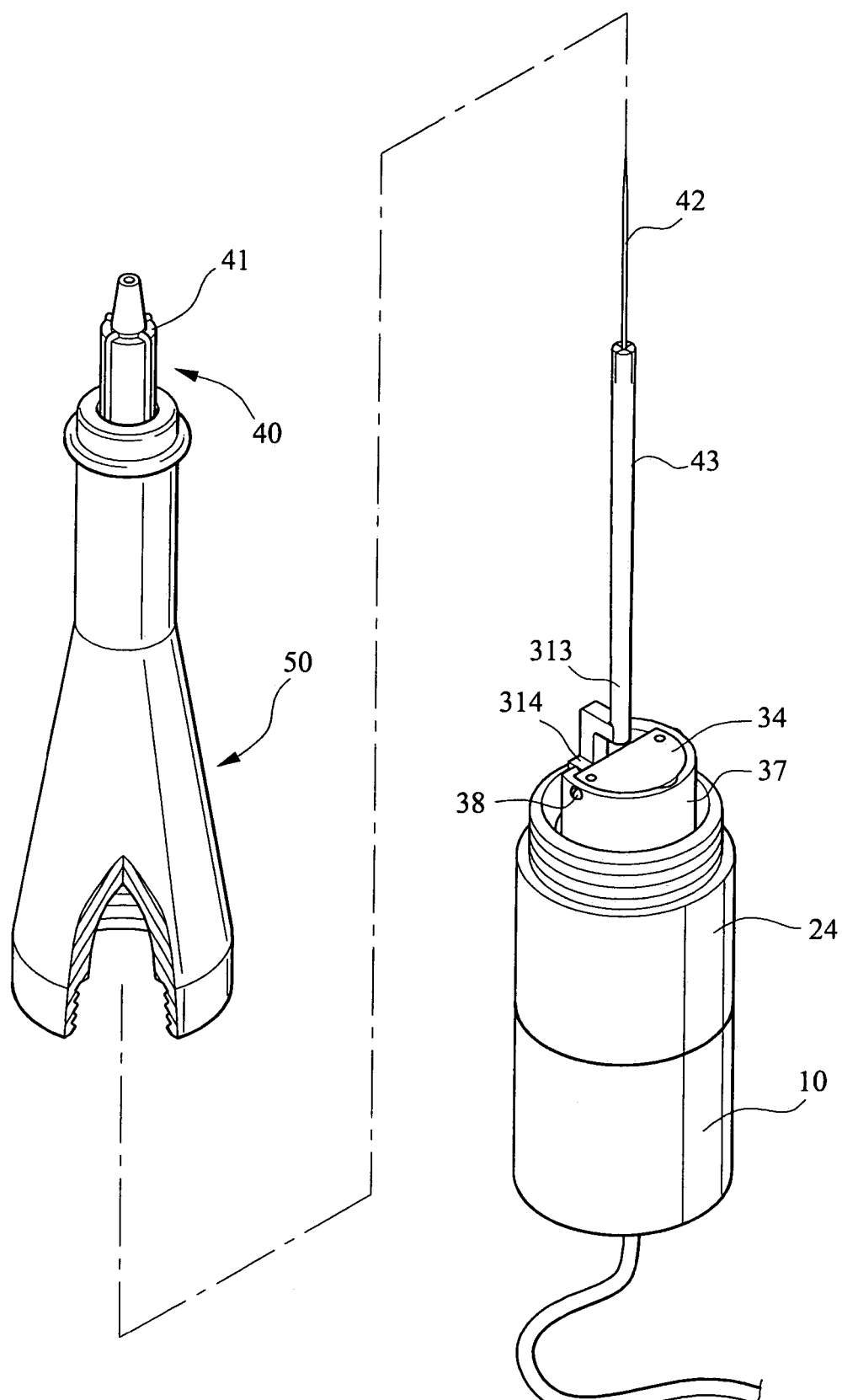
FIG. 8 is a perspective view of an eyebrow-beautifying device incorporating a second preferred embodiment of transmission system according to the invention, where the assembled needle assembly and cap are separated.
Figure 9:
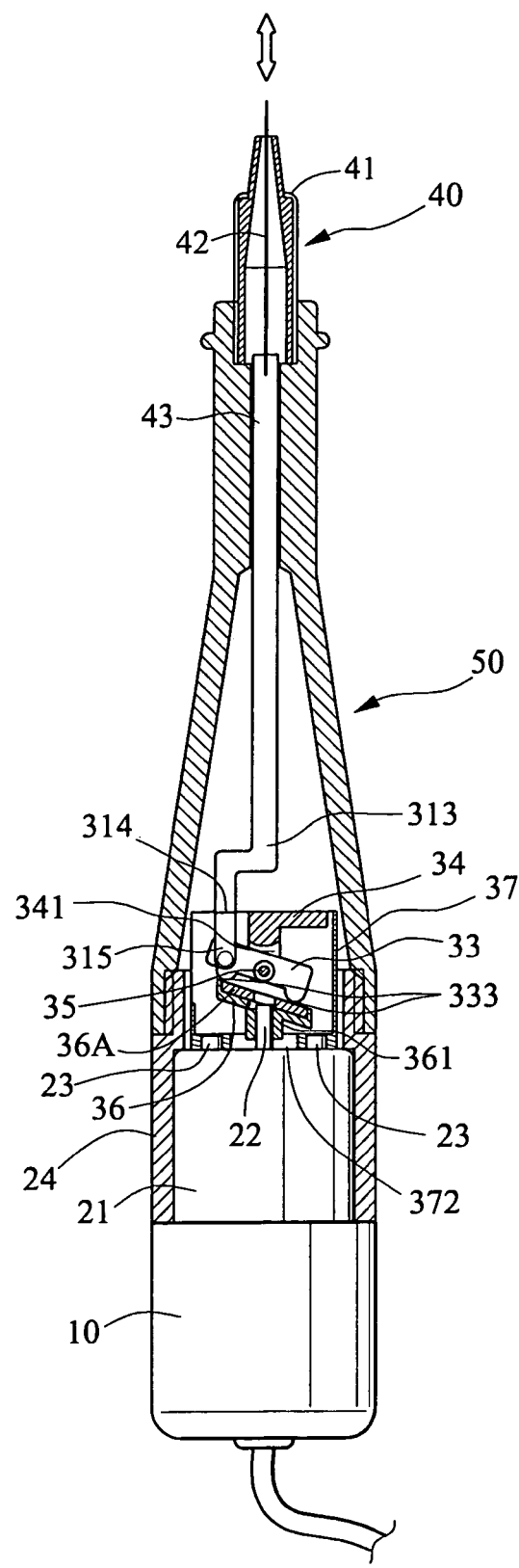
FIG. 9 is a cross-sectional view of FIG. 8.

Further note that an eyebrow-beautifying device incorporating a second preferred embodiment of transmission system in accordance with the invention is also possible as referring to FIGS. 8 and 9. The characteristics of the second preferred embodiment are detailed below. The transmission unit 31 and the post 43 in the first preferred embodiment of transmission system are formed integrally in the second preferred embodiment. The joining member 32 and the top section 311 are eliminated for simplifying the components of the eyebrow-beautifying device. In other words, the joining member 32 is not critical to the transmission system of eyebrow-beautifying device of the invention. Other components will not be described in detail below since they are the same as that described in the first preferred embodiment.

While the invention herein disclosed has been described by means of specific embodiments, numerous modifications and variations could be made thereto by those skilled in the art without departing from the scope and spirit of the invention set forth in the claims.

What is claimed is:

1. A transmission system of an eyebrow-beautifying device, comprising:
    a needle assembly including a post, a needle projected upward from the post and a top sleeve for permitting the needle to either project therefrom or retract thereinto;
    a joining member including a lower section having a longitudinal cut, the joining member being coupled to a lower portion of the post of the needle assembly;
    a substantially zigzag transmission unit including a top section coupled to the lower section of the joining member and a bottom connecting member;
    a connecting unit including two vertical sections at both sides, a horizontal section on the top, a central slot between a bottom portion of two vertical sections, and a pivot hole through a bottom of the vertical sections and the slot;
    a lever member including a first aperture, a keyhole coupled to the connecting member, and two contacts at bottoms of both sides, the lever member being pivotably disposed in the slot by inserting a pin through the pivot hole;
    a slanted seat including a lower shaft sleeve;
    a motor including a shaft projected from a top and two diametrically disposed projections on the top; and
    a cylinder having a C-shaped section and including a central hole on a bottom for permitting the shaft sleeve of the slanted seat to pass through to be fastened around the shaft of the motor, and two diametrically disposed second apertures on the bottom, the second apertures being adapted to snugly receive the projections of the motor when the cylinder is rested on the motor,
    whereby a rotation of the shaft will rotate the slanted seat for moving the transmission unit up and down cyclically and projecting the needle from the top sleeve and retract thereinto cyclically.

2. The transmission system of claim 1, wherein the cylinder further comprises two diametrically disposed recesses on an inner wall, the recesses being adapted to snugly receive the vertical sections of the connecting unit prior to threadedly securing the cylinder to the connecting unit by driving fasteners through the cylinder into the vertical sections of the connecting unit.

3. The transmission system of claim 1, wherein the bottom connecting member having a vertically oriented slit shaped section is extended laterally into the keyhole for fastening.

4. The transmission system of claim 1, wherein the transmission unit further comprises a first L-shaped section connected to the lower portion of the top section, a second L-shaped section connected to the lower portion of the first L-shaped section, a third L-shaped section connected to the lower portion of the second L-shaped section, and a bottom connecting member connected to the lower portion of the third L-shaped section in which the vertical portion of the first L-shaped section is parallel to the vertical portion of the second L-shaped section, the vertical portion of the second L-shaped section is parallel to the vertical portion of the third L-shaped section, the horizontal portion of the first L-shaped section is vertical to the horizontal portions of the second L-shaped section and the third L-shaped section wherein the bottom connecting member is integrally formed with the horizontal portion of the second L-shaped section, and the connecting member being extended laterally from a vertically oriented slit of the vertical portion of the third L-shaped section.

5. The transmission system of claim 1, wherein the contacts of the lever member rest on a periphery of the slanted seat, a pivot point of the transmission unit and the lever member is disposed above the contacts, and a torque of the lever member is substantially the same as that of the transmission unit.

6. The transmission system of claim 1, wherein the slanted seat further comprises a replaceable wear-resistant member on the slanted seat.

* * * * *